United States Patent

Connor et al.

[11] 4,056,532
[45] Nov. 1, 1977

[54] ALPHA-ARYL-2-PYRIDINEETHANOL 1-OXIDES AND ALPHA-PYRIDINYL-2-PYRIDINEETHANOL 1-OXIDES

[75] Inventors: David T. Connor, Parsippany; Patricia A. Young, Madison; Maximillian von Strandtmann, Rockaway, all of N.J.

[73] Assignee: Warner-Lambert Company, Morris Plains, N.J.

[21] Appl. No.: 699,278

[22] Filed: June 24, 1976

[51] Int. Cl.$^2$ .......................................... C07D 213/89
[52] U.S. Cl. ..................... 260/296 R; 260/295 R; 260/296 D; 260/297 R; 424/263
[58] Field of Search .......... 260/296 R, 297 R, 295 R, 260/296 D

[56] References Cited

PUBLICATIONS

Klingsberg, Pyridine and its Derivatives, Part Four, frontispage and pp. 54 to 58, Interscience Publishers (1964).
Burckhalter et al., J. Med. Chem., vol. 10, pp. 565 to 575 (1967).
Abramovitch et al., J. Org. Chem., vol. 37, pp. 1690 to 1696 (1972).
Al-Tai et al., Chemical Abstracts, vol. 69, abst. No. 106494d (1968).
Al-Tai et al., Chemical Abstracts, vol. 72, abst. No. 43,377g (1970).

Primary Examiner—Richard L. Raymond
Attorney, Agent, or Firm—Albert H. Graddis; Frank S. Chow; Anne M. Kelly

[57] ABSTRACT

Alpha-aryl-2-pyridineethanol 1-oxides and alpha-pyridinyl-2-pyridineethanol 1-oxides having the formula I or II:

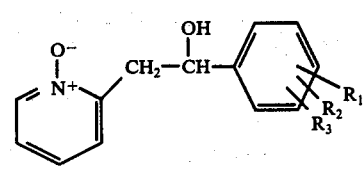

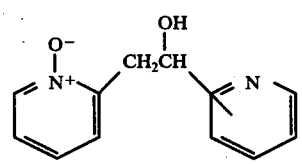

wherein $R_1$ is hydrogen, halogen, hydroxy, lower alkyl, lower alkoxy, benzyloxy, lower alkanoyloxy, ortho-amino or ortho-lower alkylamino; $R_2$ and $R_3$ are each hydrogen, halogen, hydroxy, lower alkyl, lower alkoxy, benzyloxy or lower alkanoyloxy; the pharmaceutically acceptable acid addition salts thereof and a process for the preparation thereof are described. The compounds of this invention are useful in the prevention of allergic and asthmatic reactions.

10 Claims, No Drawings

ALPHA-ARYL-2-PYRIDINEETHANOL 1-OXIDES AND ALPHA-PYRIDINYL-2-PYRIDINEETHANOL 1-OXIDES

DESCRIPTION OF THE PRIOR ART

1-Substituted-2-(2-pyridinyl)ethanone N-oxide starting materials from which the corresponding ethanol N-oxides of this invention may be prepared have been disclosed by Osborne, et al., in J. Heterocyclic Chem., No. 1:138–140 (1964) and in co-pending U.S. application Ser. No. 611,282, filed Sept. 8, 1975.

DESCRIPTION OF THE PARTICULAR EMBODIMENTS

This invention relates to alpha-aryl-2-pyridineethanol 1-oxides and alpha-pyridinyl-2-pyridineethanol 1-oxides having the formula I or II:

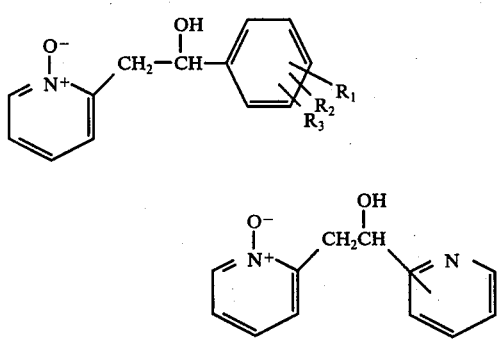

wherein $R_1$ is hydrogen, halogen, hydroxy, lower alkyl, lower alkoxy, benzyloxy, lower alkanoyloxy, ortho-amino or ortho-lower alkylamino; $R_2$ and $R_3$ are each hydrogen, halogen, hydroxy, lower alkyl, lower alkoxy, benzyloxy or lower alkanoyloxy; and the pharmaceutically acceptable acid addition salts thereof. Compounds of the formula I wherein $R_1$ is hydrogen, bromo, methoxy, methyl or ortho-amino; $R_2$ is hydrogen or methoxy; and $R_3$ is hydrogen, as well as their pharmaceutically acceptable acid addition salts, are particularly preferred.

Compounds of the invention having the formula I are prepared by reacting the corresponding ketone having the formula III:

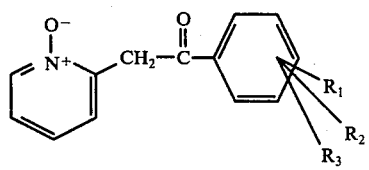

wherein $R_1$, $R_2$ and $R_3$ are as defined above in formula I, in an ice-cold, inert solvent with sodium borohydride. Typically, a solvent such as methanol may be used for this reaction.

Compounds of the invention having formula II are prepared by reacting the corresponding ketones having the formula IV:

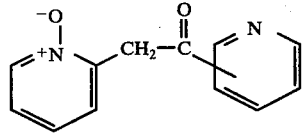

in an ice-cold, inert solvent with sodium borohydride. As in the preparation of compound I, a solvent, typically methanol, is used for this reaction.

The starting materials used for the preparation of compounds of the formula I of this invention are the ketone derivatives described in co-pending U.S. application Ser. No. 611,282, filed Sept. 8, 1975, entitled: "1-Substituted-2-(2-Pyridinyl)Ethanone N-Oxides." The starting ketone used for the preparation of alpha-(2-pyridinyl)-2-pyridineethanol 1-oxide is also described in aforementioned co-pending U.S. application Ser. No. 611,282. The starting ketones used for the synthesis of alpha-(3-pyridinyl)-2-pyridineethanol 1-oxide and alpha-(4-pyridinyl)-2-pyridineethanol 1-oxide are prepared as described by Osborne, et al., in J. Heterocyclic Chem., 1:138–140 (1964) and examplified in Examples 6 and 7 of this specification.

Pharmaceutically acceptable acid addition salts of the compounds of this invention are prepared according to conventional procedures by treating the free base form of the compounds of the invention in an alcoholic solution with the desired acid.

In the above formulas for the compounds of this invention, the R group definitions may be more fully described as follows: the term "lower alkyl" is meant to include lower aliphatic hydrocarbons having 1 to 7, preferably 1 to 4 carbon atoms in the alkyl chain, such as methyl, ethyl, propyl, isopropyl, butyl or isobutyl. This definition for lower alkyl also applies to the alkyl portions of "alkoxy" and "alkanoyl". The term "halogen" is meant to include bromine, chlorine, iodine and fluorine.

The compounds of this invention are active in the prevention of allergic conditions (typically, asthmatic reactions) in mammals such as rats and guinea pigs as evidenced by positive results in the passive cutaneous anaphylaxis screen (PCA test). The PCA screen is a modification of the procedures described by I. Mota, Life Sciences, Vol. 4, No. 7:465–474 (1963) and Z. Ovary and O. Bier, Proc. Soc, Exptl. Biol. Med., 81:584–586 (1952) and provides a measure of the effectiveness of test compounds in inhibiting the release or action of toxic products arising from the combination of reaginic antibodies with specific antigens. These toxic products are causative factors in such disorders as bronchial allergic asthma (extrinsic reagins), exercise asthma, cold asthma, hay fever, perennial allergic rhinitis, food allergies, serum or drug allergies, insect sting allergies, angio-neurotic edema, atopic dermatitis, including infantile eczema, urticaria, dermographism, dermatoconjuctivitis, acute allergic conjunctivitis, chronic allergic conjunctivitis, and the like.

Inhibition of reaginic antigen/antibody reactions in experimental animals such as rats and guinea pigs is regarded as representative of inhibition of human reaginic antigen/antibody reactions which occur during allergic episodes.

In the PCA screen, rats are sensitized with 1 mg. of ovalbumin (Pentex, Kankakee, Ill.) intramuscularly and with $10^{10}$ B. pertussis organisms (Parke-Davis and Co., Detroit, Michigan; Bio. 210) intraperitoneally. On the 14th day the animals are bled and the serum prepared in the usual manner. The reaginic nature of antiovalbumin serum thus obtained is verified by the use of standard criteria.

Passive cutaneous anaphylaxis is induced as described in Ovary and Bier (1952) and by Mota (1963). Suitable antibody concentration in 0.1 ml. to result in reactions between 7 and 19 mm. in diameter (usually 1:5 to 1:40 dilutions) are injected intradermally on either side of the dorsal midline of rats. Forty-eight hours later, the animals are dosed with drug and injected in the tail vein with 1 ml. of saline containing 0.25% Evans blue and 1 mg. ovalbumin. Thirty minutes later, animals are sacrificed with ether, the dorsal skin reflected, and the mean orthogonal diameter of the reaction site measured.

A linear relationship can be shown to exist between the relative antibody concentration and the diameter of the resultant reaction if the antibody concentration is adjusted to yield diameters between approximately 7 and 19 mm. For each experiment, a line is fitted by the least squares method for the relationship of the diameter to the relative antibody concentration. This line is extrapolated to zero antibody concentration to derive the base-line diameter. The percentage inhibition due to drug treatment is then calculated by the formula:

$$\% \text{ inhibition} = \left[1 - \frac{\text{(diameter of experimental-base value)}}{\text{(diameter of control - base value)}}\right] \times 100$$

The significance of the inhibition is measured by Student's t-test.

For administration, the compounds are suspended by trituration in 1% gum tragacanth and 0.15M saline so as to give 10 ml/kg body weight.

Thus, the compounds of this invention are active for the inhibition of reagin-mediated allergic disorders when administered to mammals in need thereof at dose levels of from about 25 to about 100 ml/kg of body weight, by the oral or parenteral route. This dosage may be varied depending upon the severity of the condition, the age, weight, sex and class of mammal being treated, as well as the route of administration. For example, alpha-(2-pyridinyl)-2-pyridineethanol 1-oxide (the compound of Example 8) shows a 58% inhibition of the allergic response at 25 mg/kg when tested, intraperitoneally, in the passive cutaneous anaphyalxis (PCA) screen. Similarly, alpha-(2-methoxy-5-methylphenyl)-2-pyridineethanol 1-oxide (the compound of Example 2) shows a 52% inhibition of the allergic response at 5 mg/kg when tested, intravenously, in the PCA screen. Consequently, the compounds of this invention are useful in the treatment of asthma, hay fever and other allergic conditions.

In use, the compounds of the invention may be combined with parenterally acceptable vehicles, such as gum tragacanth, in saline suspension, to provide dosage forms suitable for parenteral administration; or they may be combined with pharmaceutical diluents such as lactose, cornstarch, and the like and formulated into tablet or capsule dosage forms.

To further illustrate the practice of this invention, the following examples are included:

EXAMPLE 1

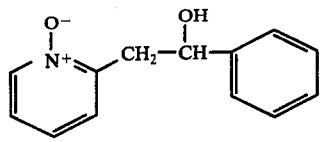

Alpha-Phenyl-2-pyridineethanol N-oxide

To an ice-cold solution of 1-phenyl-2-(2-pyridinyl)ethanone N-oxide (10.0g) in methanol (40 ml) is added sodium borohydride (1.72g). When the reaction bubbling ceases, the mixture is stirred an additional 0.5 hours at room temperature. The solvent is removed under reduced pressure to give a solid residue, which is suspended in water, filtered, washed thoroughly with water and dried at room temperature. Recrystallization from benzene gives white crystals (7.80g, 77%), mp. 121°–123° C.

Anal. Calcd. for $C_{13}H_{13}NO_2$: C, 72.54; H, 6.09; N, 6.51. Found: C, 72.56; H, 6.37; N, 6.44.

EXAMPLE 2

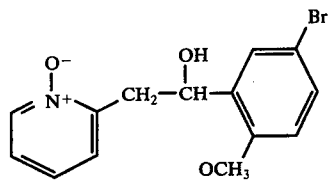

Alpha-(5-bromo-2-methoxyphenyl)-2-pyridineethanol N-oxide

Prepared by the procedure described in Example 1 using 1-(5-bromo-2-methoxyphenyl)-2-(2-pyridinyl)ethanone N-oxide (6.0g). Recrystallization from ethyl acetate gives white crystals (5.04g, 83%), mp. 155°–157° C.

Anal. Calcd. for $C_{14}H_{14}BrNO_3$: C, 51.86; H, 4.35; N, 4.32; Br, 24.64. Found: C, 51.66; H, 4.40; N, 4.19; Br, 24.79.

EXAMPLE 3

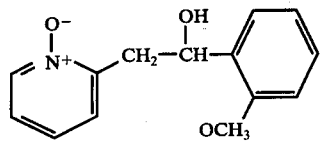

Alpha-(2-methoxyphenyl)-2-pyridineethanol 1-oxide

Prepared by the procedure described in Example 1 using 1-(2-methoxyphenyl)-2-(2-pyridinyl)ethanone N-oxide (15.0g). Recrystallization from ethyl acetate gives white crystals (13.5g, 89%), mp. 142°–143° C.

Anal. Calcd. for $C_{14}H_{15}NO_3$: C, 68.55; H, 6.16; N, 5.71. Found: C, 68.49; H, 6.22; N, 5.51.

EXAMPLE 4

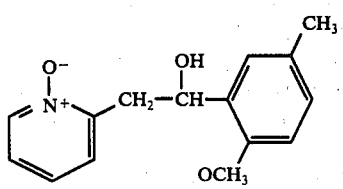

Alpha-(2-methoxy-5-methylphenyl)-2-pyridineethanol 1-oxide

Prepared by the procedure described in Example 1 from 1-(2-methoxy-5-methylphenyl)-2-(2-pyridinyl)ethanone N-oxide (5.0g). Recrystallization from ethyl acetate gives off-white crystals (2.67, 53%), mp. 118°–119° C.

Anal. Calcd. for $C_{15}H_{17}NO_3$: C, 69.48; H, 6.61; N, 5.40. Found: C, 69.18; H, 6.74; N, 5.36.

EXAMPLE 5

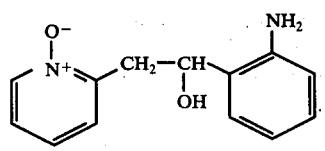

Alpha-(2-Aminophenyl)-2-pyridineethanol 1-oxide

Prepared by the method described in Example 1 from 1-(2-aminophenyl)-2-(2-pyridinyl) ethanone N-oxide (4.0g, 0.0175m). Recrystallization from absolute ethanol gives white crystals (2.3g, 56%), mp. 175°–176.5° C.

Anal. Calcd. for $C_{13}H_{14}N_2O_2$: C, 67.81; H, 6.13; N, 12.17. Found: C, 67.73; H, 6.14; N, 12.31.

EXAMPLE 6

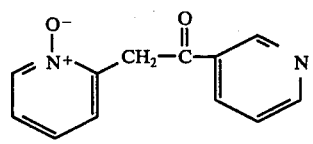

1-(3-pyridinyl)-2-(2-pyridinyl)ethanone N-(2-pyridinyl)oxide[1]

[1] D. R. Osborne and R. Levine, *J. Heterocyclic Chem.*, 138 (1964).

2-Picoline N-oxide (43.0g, 0.39m) is added to sodium amide (15.2g, 0.39m) in anhydrous liquid ammonia (500ml). The resulting anion is stirred for 1 hour and then ethyl nicotinate (30g, 0.2m) is added dropwise. The reaction mixture is stirred 1 hour and then quenched by the addition of solid ammonium chloride (25g, 0.46m). The ammonia is allowed to evaporate at room temperature. The remaining water soluble sludge is dissolved in boiling ethyl acetate and the insoluble salts are filtered off. On standing, the product crystallizes out and recrystallization from ethyl acetate gives white crystals (10.8g, 25.4%), mp. 140°–143° C.

Anal. Calcd. for $C_{12}H_{10}N_2O_2$: C, 67.28; H, 4.71; N, 13.08. Found: C, 67.04; H, 4.71; N, 13.02.

EXAMPLE 7

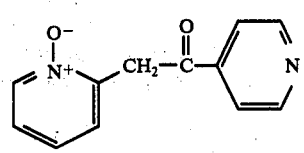

1-(4-pyridinyl)-2-(2-pyridinyl)ethanone N-(2-pyridinyl)oxide

Prepared by the method described in Example 6 from ethyl isonicotinate and 2-picoline N-oxide anion. Recrystallization from ethyl acetate gives brownish, yellow-green crystals (3.55g, 10%), mp. 110°–112° C.

Anal. Calcd. for $C_{12}H_{10}N_2O_2$: C, 67.28; H, 4.71; N, 13.08. Found: C, 67.01; H, 4.72; N, 13.00.

EXAMPLE 8

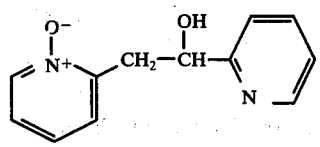

Alpha-(2-pyridinyl)-2-pyridineethanol 1-oxide

Prepared by the procedure described in Example 1 from 1,2(N-oxide)-dipyridinylethanone (4.38g). Removal of solvent leaves a viscous oil which is partitioned between water and chloroform. The aqueous is extracted three times with fresh portions of chloroform. The extracts are combined, dried over sodium sulfate and evaporated to a solid product. Recrystallization from ethyl acetate gives white crystals (2.82g, 64%), mp. 145°–147° C.

Anal. Calcd. for $C_{12}H_{12}N_2O_2$: C, 66.65; H, 5.59; N, 12.96. Found: C, 66.47; H, 5.57; N, 12.84.

EXAMPLE 9

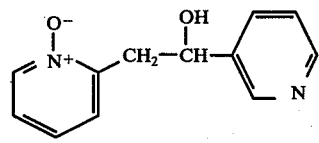

Alpha-(2-pyridinyl)-3-pyridineethanol 1-oxide

Prepared by the procedure described in Example 8 from 1-(3-pyridinyl)-2-(2-pyridinyl) ethanone N-(2-pyridinyl)oxide (3.50g). Recrystallization from ethyl acetate gives white crystals (1.75g. 49.6%), mp. 147°–150° C.

Anal. Calcd. for $C_{12}H_{12}N_2O_2$: C, 66.65; H, 5.59; N, 12.96. Found: C, 66.29; H, 5.76; N, 12.89.

EXAMPLE 10

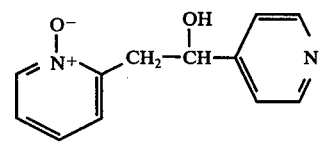

Alpha-(2-pyridinyl)-4-pyridineethanol 1-oxide

Prepared by the procedure described in Example 8 from 1-(4-pyridinyl)-2-(2-pyridinyl) ethanone N-(2-pyridinyl)oxide (4.0g). Recrystallization from ethyl acetate gives white crystals (2.00g, 49.6%), mp. 111°–113° C.

Anal. Calcd. for $C_{12}H_{12}N_2O_2$: C, 66.65; H, 5.59; N, 12.96. Found: C, 66.47; H, 5.69; N, 12.87.

We claim:

1. A compound of the formula I or II:

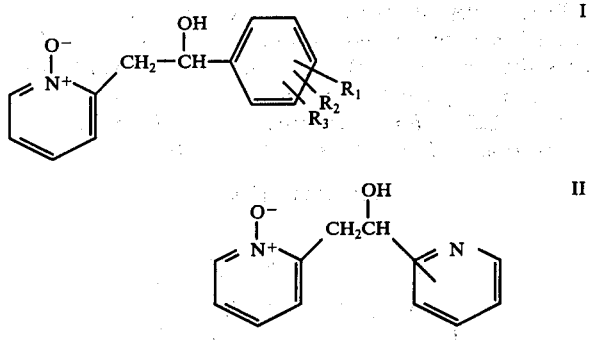

wherein $R_1$ is hydrogen, halogen, hydroxy, lower alkyl, lower alkoxy, benzyloxy, lower alkanoyloxy, ortho-amino or ortho-lower alkylamino; $R_2$ and $R_3$ are each hydrogen, halogen, hydroxy, lower alkyl, lower alkoxy, benzyloxy or lower alkanoyloxy, and the pharmaceutically acceptable acid addition salts thereof.

2. The compound of the formula I, according to claim 1, wherein $R_1$ is hydrogen, bromo, methoxy, methyl or ortho-amino; $R_2$ is hydrogen or methoxy; and $R_3$ is hydrogen; and the pharmaceutically acceptable acid addition salts thereof.

3. The compound according to claim 1 which is alpha-phenyl-2-pyridineethanol N-oxide.

4. The compound according to claim 1 which is alpha-(5-bromo-2-methoxyphenyl)-2-pyridineethanol N-oxide.

5. The compound according to claim 1 which is alpha-(2-methoxyphenyl)-2-pyridineethanol 1-oxide.

6. The compound according to claim 1 which is alpha-(2-methoxy-5-methylphenyl)-2-pyridineethanol 1-oxide.

7. The compound according to claim 1 which is alpha-(2-aminophenyl)-2-pyridineethanol 1-oxide.

8. The compound according to claim 1 which is alpha-(2-pyridinyl)-2-pyridineethanol 1-oxide.

9. The compound according to claim 1 which is alpha-(2-pyridinyl)-3-pyridineethanol 1-oxide.

10. The compound according to claim 1 which is alpha-(2-pyridinyl)-4-pyridineethanol 1-oxide.

* * * * *